US012758503B2

(12) United States Patent
Cho et al.

(10) Patent No.: US 12,758,503 B2

(45) Date of Patent: Oct. 13, 2026

(54) PHARMACEUTICAL FORMULATION COMPRISING CIBENZOLINE OR SALT THEREOF

(71) Applicant: CELLTRION INC., Incheon (KR)

(72) Inventors: Kyung Suk Cho, Chungcheongbuk-do (KR); GuK Bin Park, Chungcheongbuk-do (KR); Jae Hun Song, Chungcheongbuk-do (KR); Byung Kwan Moon, Chungcheongbuk-do (KR); Hoon Namkoong, Incheon (KR); Ha Young Choi, Incheon (KR); Bon Joong Kim, Incheon (KR); Woo Hyong Cho, Chungcheongbuk-do (KR); Da Wo Jeong, Chungcheongbuk-do (KR); Soo Bin Jang, Chungcheongbuk-do (KR)

(73) Assignee: CELLTRION INC., Incheon (KR)

( * ) Notice: Subject to any disclaimer, the term of this patent is extended or adjusted under 35 U.S.C. 154(b) by 822 days.

(21) Appl. No.: 17/780,898

(22) PCT Filed: Dec. 17, 2020

(86) PCT No.: PCT/KR2020/018526

§ 371 (c)(1),
(2) Date: May 27, 2022

(87) PCT Pub. No.: WO2021/125824

PCT Pub. Date: Jun. 24, 2021

(65) Prior Publication Data

US 2023/0040902 A1 Feb. 9, 2023

(30) Foreign Application Priority Data

Dec. 19, 2019 (KR) ........................ 10-2019-0170504

(51) Int. Cl.
*A61K 9/24* (2006.01)

(52) U.S. Cl.
CPC .................................... *A61K 9/209* (2013.01)

(58) Field of Classification Search
CPC ...................................................... A61K 9/209
See application file for complete search history.

(56) References Cited

U.S. PATENT DOCUMENTS

| | | | | |
|---|---|---|---|---|
| 5,393,765 A * | 2/1995 | Infeld | A61K 9/2018 424/464 |
| 6,372,255 B1 * | 4/2002 | Saslawski | A61K 9/209 424/469 |
| 9,180,101 B2 | 11/2015 | Oh et al. | |
| 2002/0098232 A1 | 7/2002 | Midha et al. | |
| 2013/0095180 A1 | 4/2013 | Lee et al. | |

FOREIGN PATENT DOCUMENTS

| | | |
|---|---|---|
| EP | 1041972 | 9/2002 |
| JP | 2010/132561 | 6/2010 |
| KR | 10-2011-0103113 | 9/2011 |
| KR | 10-2012-0083276 | 7/2012 |
| KR | 10-2013-0032316 | 4/2013 |
| WO | PCT/KR2020/018526 | 4/2021 |

OTHER PUBLICATIONS

Takehana, S. et al., Cardiovascular effects of optical isomers of cibenzoline, assessed in the canine isolate, blood-perfused papillary muscle and sinotrial node preparations, Journal of Cardiovascular Pharmacology, 1999, vol. 34, 660-665 (Year: 1999).*
Anonymous, Methocel K100 LV Safety Data Sheet, Dupont, 2022 (Year: 2022).*
Campos-Aldrete, M.E. et al., Influence of the viscosity grade and the particle size of HPMC on metronidazole release from matrix tablets, European Journal of Pharmaceutics and Biopharmaceutics, 1997, vol. 43, 173-178 (Year: 1997).*
Davis, T.C. et al., Improving patient understanding of prescription drug label instructions, Journal of General Internal Medicine, 2008 , vol. 24, 57-62 (Year: 2008).*
Kiran et al., "Bilayer Tablets—A Review", International Journal of Pharmaceutical, Chemical and Biological Sciences, 2015, United Kingdom, pp. 510-516.
Hamada et al., "Antiarrhythmic Drug, Cibenzoline, can Directly Improve the Left Ventricular Diastolic Function in Patients with Hypertrophic Cardiomyopathy", Japanese Circulation Journal vol. 65, Jun. 2001, Japan, pp. 531-538.

(Continued)

*Primary Examiner* — Bethany P Barham
*Assistant Examiner* — Paul Hoerner
(74) *Attorney, Agent, or Firm* — Wells St. John P.S.

(57) ABSTRACT

A pharmaceutical formulation including an immediate release layer and an extended release layer according to the present disclosure has a biphasic dissolution profile, such that it is possible to quickly reach an effective plasma concentration of cibenzoline at the early stage, and the effective plasma concentration may be continuously maintained at the late stage. Therefore, the medicinal effect of cibenzoline may be maintained only by an administration of a single formulation once a day.

12 Claims, 2 Drawing Sheets

(56) References Cited

OTHER PUBLICATIONS

Takehana et al., "Cardiovascular Effects of Optical Isomers of Cibenzoline, Assessed in the Canine Isolated, Blood-Perfused Papillary Muscle and Sinoatrial Node Preparations", Journal of Cardiovascular Pharmacology vol. 34, Nov. 1999, pp. 660-665, available online at https://journals.lww.com/cardiovascularpharm/Fulltext/1999/11000/Cardiovascular_Effects_of_Optical_Isomers_of.6.aspx.
Coppini et al., "Late Sodium Current Inhibition Reverses Electromechanical Dysfunction in Human Hypertrophic Cardiomyopathy", Circulation, Feb. 2013, United States, pp. 575-584.
Johannesen et al., "Late Sodium Current Block for Drug-Induced Long QT Syndrome: Results From a Prospective Clinical Trial", Clinical Pharmacology & Therapeutics vol. 99, No. 2, Feb. 2016, United States, pp. 214-223.

* cited by examiner

[FIG. 1]
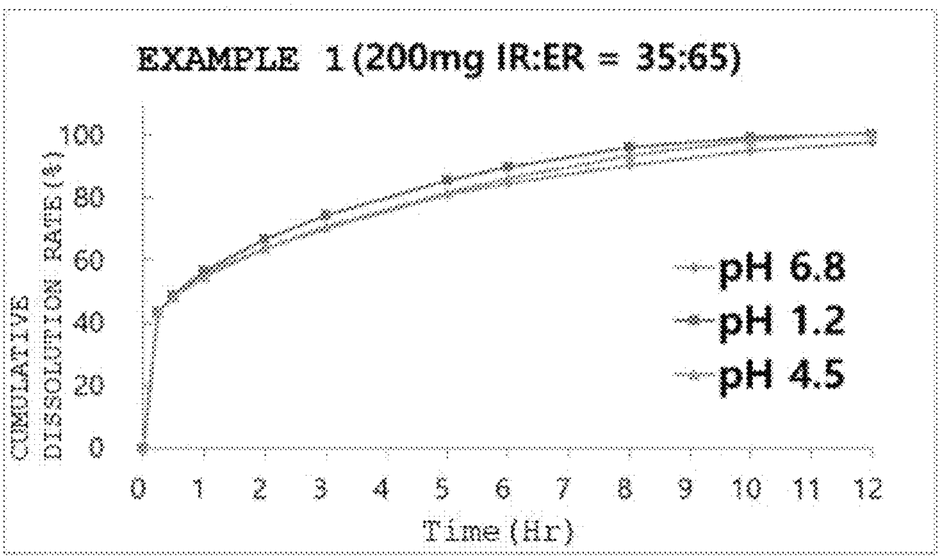
[FIG. 2]
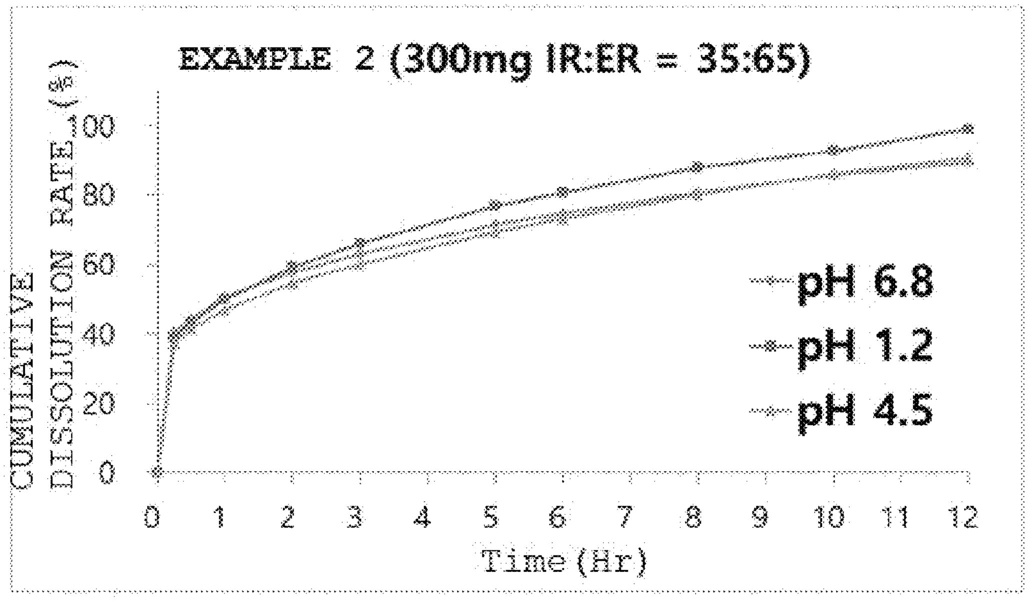

[FIG. 3]
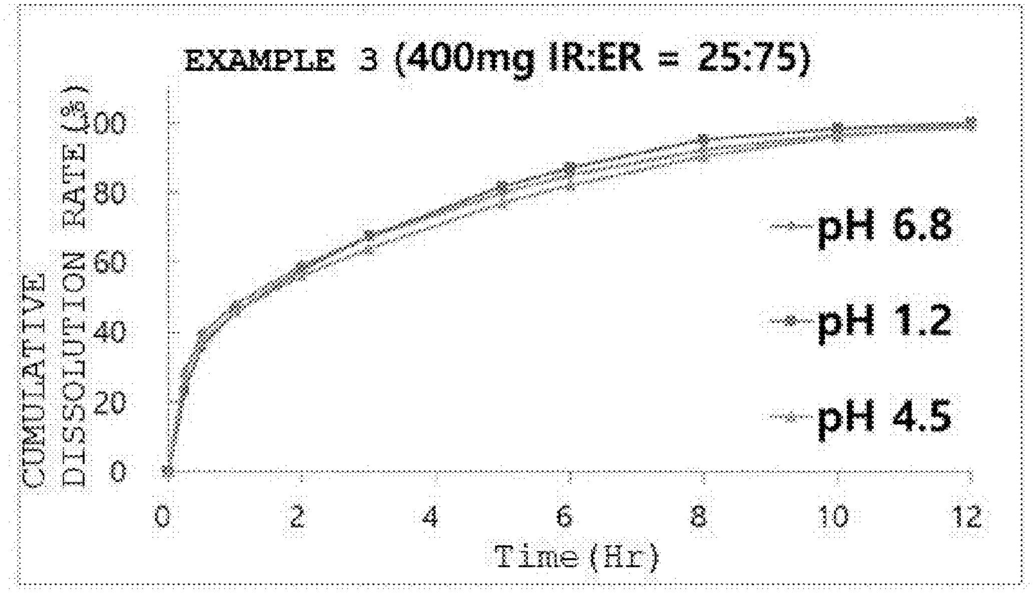

PHARMACEUTICAL FORMULATION COMPRISING CIBENZOLINE OR SALT THEREOF

RELATED PATENT DATA

This application is a 35 U.S.C. § 371 of and claims priority to PCT International Application No. PCT/KR2020/018526, filed 17 Dec. 2020, which claims priority to KR Application No. 10-2019-0170504, filed 19 Dec. 2019, each of which is incorporated herein by reference.

TECHNICAL FIELD

The present disclosure relates to a pharmaceutical composition comprising cibenzoline or a salt thereof, and relates to a pharmaceutical formulation comprising cibenzoline or a salt thereof, in which the pharmaceutical formulation includes an immediate release layer and an extended release layer.

BACKGROUND ART

Cibenzoline (cifenline, 2-(2,2-diphenylcyclopropyl)-4,5-dihydro-1H-imidazole, 53267-01-9 (CAS number)) is a compound having a structure of the following Chemical Formula 1, and is a drug used as an antiarrhythmic agent which is a Group 1 sodium channel blocker. In addition, the effects of cibenzoline as a calcium channel blocker and a potassium channel blocker are also known.

[Chemical Formula 1]

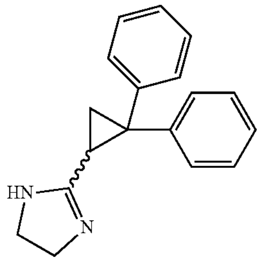

The cibenzoline rapidly disappears after the drug is absorbed into a human body due to its short half-life, and thus, it should be administered a few times a day because of its short duration of medicinal effect. Cibenzoline has been currently developed and marketed in the form of a tablet for treating arrhythmia and has been administered three times a day.

Therefore, there is a need to develop an extended release tablet that increases a medication compliance of a patient by reducing the number of doses and continuously maintains medicinal effect by continuously maintaining a plasma concentration of a drug.

However, a conventionally developed single extended release tablet has a disadvantage in that it takes a long time to reach an effective plasma concentration at the early stage. Thus, it is difficult to continuously maintain effective pharmacological activity for 24 hours while expressing rapid pharmacological activity after oral administration.

Therefore, there is a need to develop a formulation for solving the disadvantages of the extended release tablet by reaching an effective plasma concentration at the early stage in a short period of time while having an advantage of the extended release tablet in maintaining the plasma concentration of the drug.

DISCLOSURE

Technical Problem

An object of the present disclosure is to provide a pharmaceutical formulation comprising S(−)-cibenzoline or a pharmaceutically acceptable salt thereof, in which the pharmaceutical formulation includes an immediate release layer and an extended release layer.

Technical Solution

The present disclosure provides a pharmaceutical formulation comprising about 150 to about 450 mg of S(−)-cibenzoline or a pharmaceutically acceptable salt thereof, in which the pharmaceutical formulation includes an immediate release layer and an extended release layer. The pharmaceutical formulation may comprise about 150 mg, about 200 mg, about 250 mg, about 300 mg, or about 400 mg of S(−)-cibenzoline or a pharmaceutically acceptable salt thereof.

In one embodiment of the present disclosure, in the pharmaceutical formulation, a weight ratio of the S(−)-cibenzoline or the pharmaceutically acceptable salt thereof contained in the immediate release layer to the S(−)-cibenzoline or the pharmaceutically acceptable salt thereof contained in the extended release layer may be about 1:4 to about 1:1. (In this specification, the ratio of A to B means the ratio of A:B.) The weight ratio may be about 1:3 to about 1:1, about 3:7 to about 1:1, about 1:2 to about 1:1, about 7:13 to about 1:1, about 2:3 to about 1:1, about 9:11 to about 1:1, about 1:4 to 9:11, about 1:3 to about 9:11, about 3:7 to about 9:11, about 7:13 to about 9:11, about 2:3 to about 9:11, about 1:4 to 2:3, about 1:3 to about 2:3, about 3:7 to about 2:3, about 7:13 to about 2:3, about 1:4 to 7:13, about 1:3 to about 7:13, about 3:7 to about 7:13, about 1:4 to 3:7, about 1:3 to about 3:7, or about 1:4 to about 1:3.

In one embodiment of the present disclosure, an extended release agent may be contained in the pharmaceutical formulation in an amount of 5 to 30% with respect to the total weight of the extended release layer. An extended release agent may be contained in the pharmaceutical formulation in an amount of 6 to 30% or 7 to 30% with respect to the total weight of the extended release layer.

In one embodiment of the present disclosure, a viscosity of the extended release agent in the pharmaceutical formulation may be about 1,500 to about 200,000 centipoise (cps). The viscosity of the extended release agent may be about 1,550 to about 200,000, about 1,600 to about 200,000 centipoise (cps), about 1,500 to about 180,000 centipoise (cps), about 1,550 to about 180,000, about 1,600 to about 180,000 centipoise (cps), about 1,500 to about 10,000 centipoise (cps), about 1,550 to about 150,000, or about 1,600 to about 150,000 centipoise (cps). The viscosity is a value measured by the test method recommended by United States Pharmacopeia (USP).

In one embodiment of the present disclosure, the extended release agent may be selected from hydroxyethyl cellulose, hydroxypropyl methylcellulose, and a salt or derivative thereof, polyethylene oxide and a salt or derivative thereof, sodium carboxymethyl cellulose, carbomer, polyvinyl acetate, and a mixture thereof.

In one embodiment of the present disclosure, the immediate release layer of the pharmaceutical formulation may contain a disintegrant.

In one embodiment of the present disclosure, a disintegrant may be contained in the pharmaceutical formulation in an amount of about 1 to about 10% with respect to the total weight of the immediate release layer. A disintegrant may be contained in the pharmaceutical formulation in an amount of about 1 to about 5% with respect to the total weight of the extended release layer.

In one embodiment of the present disclosure, the disintegrant may be selected from carboxymethylcellulose calcium, pregelatinized starch, sodium starch glycolate, crospovidone (polyplasdone), croscarmellose sodium, low-substituted hydroxypropylcellulose, alginic acid, powdered cellulose, starch, sodium alginate, and a mixture thereof.

In one embodiment of the present disclosure, the immediate release layer of the pharmaceutical formulation may contain (a-1) S(−)-cibenzoline or a pharmaceutically acceptable salt thereof and (a-2) a disintegrant selected from carboxymethylcellulose calcium, pregelatinized starch, sodium starch glycolate, crospovidone (polyplasdone), croscarmellose sodium, low-substituted hydroxypropylcellulose, alginic acid, powdered cellulose, starch, sodium alginate, and a mixture thereof in the entire immediate release layer.

In one embodiment of the present disclosure, the extended release layer of the pharmaceutical formulation may contain (b-1) S(−)-cibenzoline or a pharmaceutically acceptable salt thereof and (b-2) an extended release agent selected from hydroxyethyl cellulose, hydroxypropyl methylcellulose, and a salt or derivative thereof, polyethylene oxide and a salt or derivative thereof, sodium carboxymethyl cellulose, carbomer, polyvinyl acetate, and a mixture thereof.

In one embodiment of the present disclosure, the immediate release layer of the pharmaceutical formulation may contain (a-1) S(−)-cibenzoline or a pharmaceutically acceptable salt thereof in an amount of about 25 to about 40% with respect to the total weight of the immediate release layer, and (a-2) a disintegrant selected from carboxymethylcellulose calcium, pregelatinized starch, sodium starch glycolate, crospovidone(polyplasdone), croscarmellose sodium, low-substituted hydroxypropylcellulose, alginic acid, powdered cellulose, starch, sodium alginate, and a mixture thereof in an amount of about 1 to about 10% with respect to the total weight of the immediate release layer.

In one embodiment of the present disclosure, the extended release layer of the pharmaceutical formulation may contain (b-1) S(−)-cibenzoline or a pharmaceutically acceptable salt thereof in an amount of about 30 to about 40% with respect to the total weight of the extended release layer, and (b-2) an extended release agent selected from hydroxyethyl cellulose, hydroxypropyl methylcellulose, and a salt or derivative thereof, polyethylene oxide and a salt or derivative thereof, sodium carboxymethyl cellulose, carbomer, polyvinyl acetate, and a mixture thereof in an amount of about 5 to about 30% with respect to the total weight of the extended release layer.

In one embodiment of the present disclosure, the immediate release layer of the pharmaceutical formulation may contain (a-1) S(−)-cibenzoline or a pharmaceutically acceptable salt thereof and (a-2) a disintegrant selected from carboxymethylcellulose calcium, pregelatinized starch, sodium starch glycolate, crospovidone (polyplasdone), croscarmellose sodium, low-substituted hydroxypropylcellulose, alginic acid, powdered cellulose, starch, sodium alginate, and a mixture thereof in the entire immediate release layer, and the extended release layer may contain (b-1) S(−)-cibenzoline or a pharmaceutically acceptable salt thereof and (b-2) an extended release agent selected from hydroxyethyl cellulose, hydroxypropyl methylcellulose, and a salt or derivative thereof, polyethylene oxide and a salt or derivative thereof, sodium carboxymethyl cellulose, carbomer, polyvinyl acetate, and a mixture thereof.

In one embodiment of the present disclosure, the immediate release layer of the pharmaceutical formulation may contain (a-1) S(−)-cibenzoline or a pharmaceutically acceptable salt thereof in an amount of about 25 to about 40% with respect to the total weight of the immediate release layer, and (a-2) a disintegrant selected from carboxymethylcellulose calcium, pregelatinized starch, sodium starch glycolate, crospovidone (polyplasdone), croscarmellose sodium, low-substituted hydroxypropylcellulose, alginic acid, powdered cellulose, starch, sodium alginate, and a mixture thereof in an amount of about 1 to about 10% with respect to the total weight of the immediate release layer, and the extended release layer may contain (b-1) S(−)-cibenzoline or a pharmaceutically acceptable salt thereof in an amount of about 30 to about 40% with respect to the total weight of the extended release layer, and (b-2) an extended release agent selected from hydroxyethyl cellulose, hydroxypropyl methylcellulose, and a salt or derivative thereof, polyethylene oxide and a salt or derivative thereof, sodium carboxymethyl cellulose, carbomer, polyvinyl acetate, and a mixture thereof in an amount of about 5 to about 30% with respect to the total weight of the extended release layer.

In one embodiment of the present disclosure, the immediate release layer or the extended release layer of the pharmaceutical formulation may contain an excipient selected from microcrystalline cellulose, lactose monohydrate, hydroxypropylcellulose, magnesium stearate, colloidal silicon dioxide, lactose, dextrin, mannitol, sorbitol, microcrystalline cellulose, calcium hydrogen phosphate, anhydrous calcium hydrogen phosphate, calcium carbonate, saccharides, polyvinylpyrrolidone, copovidone, gelatin, starch, sucrose, methyl cellulose, ethyl cellulose, light anhydrous silicic acid, talc, stearic acid, and a mixture thereof.

In one embodiment of the present disclosure, the pharmaceutical formulation may satisfy a biphasic dissolution profile in a dissolution test.

In one embodiment of the present disclosure, the pharmaceutical formulation may satisfy the following biphasic dissolution profile:

1) about 30 to about 50% of the total weight of the S(−)-cibenzoline or the pharmaceutically acceptable salt thereof is released within about 30 minutes, and
2) thereafter, a release of about 90% or more of the total weight of the S(−)-cibenzoline or the pharmaceutically acceptable salt thereof is achieved within about 12 hours.

The dissolution profile may additionally satisfy the following dissolution profile:

1) about 30 to about 50% of the total weight of the S(−)-cibenzoline or the pharmaceutically acceptable salt thereof is released within about 15 minutes, and
2) thereafter, a release of about 80% or more of the total weight of the S(−)-cibenzoline or the pharmaceutically acceptable salt thereof is achieved within about 12 hours.

In one embodiment of the present disclosure, the pharmaceutical formulation may satisfy the following dissolution profile:

1) about 30 to about 50% of the total weight of the S(−)-cibenzoline or the pharmaceutically acceptable salt thereof is released within about 30 minutes,
2) thereafter, a release of about 60% or more and about 75% or less of the total weight of the S(−)-cibenzoline or the pharmaceutically acceptable salt thereof is achieved within about 3 hours, and
3) thereafter, a release of about 90% or more of the total weight of the S(−)-cibenzoline or the pharmaceutically acceptable salt thereof is achieved within about 12 hours.

The dissolution profile may additionally satisfy the following dissolution profile:

1) about 30 to about 50% of the total weight of the S(−)-cibenzoline or the pharmaceutically acceptable salt thereof is released within about 15 minutes,
2) thereafter, a release of about 55% or more and about 75% or less of the total weight of the S(−)-cibenzoline or the pharmaceutically acceptable salt thereof is achieved within about 3 hours, and
3) thereafter, a release of about 80% or more of the total weight of the S(−)-cibenzoline or the pharmaceutically acceptable salt thereof is achieved within about 12 hours.

In one embodiment of the present disclosure, in the pharmaceutical formulation, a plasma concentration [C] of the S(−)-cibenzoline or the pharmaceutically acceptable salt thereof may be about 150 ng/mL or more for about 6 hours to about 18 hours out of 24 hours. In addition, the plasma concentration [C] of the S(−)-cibenzoline may be about 100 ng/mL or more for 24 hours. In one embodiment of the present disclosure, a minimum plasma concentration within the above time range appears even when the formulation is administered once a day.

In one embodiment of the present disclosure, Cmax of the pharmaceutical formulation may be about 280 to about 420 ng/mL when the pharmaceutical formulation is administered as a single dose of 200 mg once a day.

In one embodiment of the present disclosure, Cmax of the pharmaceutical formulation may be about 430 to about 570 ng/mL when the pharmaceutical formulation is administered as a single dose of 300 mg once a day.

In one embodiment of the present disclosure, AUC of the pharmaceutical formulation may be about 1,890 to about 2,830 ng·hr/mL over a period of 24 hours when the pharmaceutical formulation is administered as a single dose of 200 mg once a day.

In one embodiment of the present disclosure, AUC of the pharmaceutical formulation may be about 3,390 to about 4,330 ng·hr/mL over a period of 24 hours when the pharmaceutical formulation is administered as a single dose of 300 mg once a day.

In one embodiment of the present disclosure, the immediate release layer of the pharmaceutical formulation may contain (a-1) S(−)-cibenzoline or a pharmaceutically acceptable salt thereof in an amount of about 20 to about 50% with respect to the total weight of the immediate release layer, (a-2) a disintegrant in an amount of about 1 to about 10% with respect to the total weight of the immediate release layer when the immediate release layer contains or does not contain the disintegrant, (a-3) a binder in an amount of about 0.5 to about 5% with respect to the total weight of the immediate release layer, (a-4) a lubricant in an amount of about 0.1 to about 3% with respect to the total weight of the immediate release layer, and (a-5) an excipient in an amount of about 40 to about 60% with respect to the total weight of the immediate release layer.

In one embodiment of the present disclosure, the extended release layer of the pharmaceutical formulation may contain (b-1) S(−)-cibenzoline or a pharmaceutically acceptable salt thereof in an amount of about 20 to about 50% with respect to the total weight of the extended release layer, (b-2) an extended release agent in an amount of about 5 to about 30% with respect to the total weight of the extended release layer, (b-3) a binder in an amount of about 1 to about 10% with respect to the total weight of the extended release layer, (b-4) a lubricant in an amount of about 0.1 to about 3% with respect to the total weight of the extended release layer, and (b-5) an excipient in an amount of about 40 to about 60% with respect to the total weight of the extended release layer.

In one embodiment of the present disclosure, the immediate release layer of the pharmaceutical formulation may contain (a-1) S(−)-cibenzoline or a pharmaceutically acceptable salt thereof in an amount of about 30 to about 50% with respect to the total weight of the immediate release layer, (a-2) a disintegrant in an amount of about 1 to about 5% with respect to the total weight of the immediate release layer, (a-3) a binder in an amount of about 0.5 to about 2% with respect to the total weight of the immediate release layer, (a-4) a lubricant in an amount of about 0.1 to about 3% with respect to the total weight of the immediate release layer, and (a-5) an excipient in an amount of about 40 to about 60% with respect to the total weight of the immediate release layer.

In one embodiment of the present disclosure, the extended release layer of the pharmaceutical formulation may contain (b-1) S(−)-cibenzoline or a pharmaceutically acceptable salt thereof in an amount of about 20 to about 40% with respect to the total weight of the extended release layer, (b-2) an extended release agent in an amount of about 10 to about 20% with respect to the total weight of the extended release layer, (b-3) a binder in an amount of about 1 to about 10% with respect to the total weight of the extended release layer, (b-4) a lubricant in an amount of about 0.1 to about 3% with respect to the total weight of the extended release layer, and (b-5) an excipient in an amount of about 40 to about 60% with respect to the total weight of the extended release layer.

In one embodiment of the present disclosure, the immediate release layer of the pharmaceutical formulation may contain (a-1) S(−)-cibenzoline or a pharmaceutically acceptable salt thereof in an amount of about 23 to about 29% with respect to the total weight of the immediate release layer, may not contain (a-2) a disintegrant, and may contain (a-3) a binder, (a-4) a lubricant, and (a-5) an excipient in an amount of about 69 to about 71% with respect to the total weight of the immediate release layer.

In one embodiment of the present disclosure, the extended release layer may contain (b-1) S(−)-cibenzoline or a pharmaceutically acceptable salt thereof in an amount of about 33 to about 39% with respect to the total weight of the extended release layer, (b-2) an extended release agent in an amount of about 9 to about 10% with respect to the total weight of the extended release layer, and (a-3) a binder, (a-4) a lubricant, and (a-5) an excipient in an amount of about 49 to about 51% with respect to the total weight of the extended release layer.

In one embodiment of the present disclosure, the immediate release layer of the pharmaceutical formulation may contain (a-1) S(−)-cibenzoline or a pharmaceutically acceptable salt thereof in an amount of about 38 to about 42% with respect to the total weight of the immediate release layer, (a-2) a disintegrant in an amount of about 1.2 to about 5% with respect to the total weight of the immediate release layer, and (a-3) a binder, (a-4) a lubricant, and (a-5) an excipient in an amount of about 41 to about 53% with respect to the total weight of the immediate release layer.

In one embodiment of the present disclosure, the extended release layer may contain (b-1) S(−)-cibenzoline or a pharmaceutically acceptable salt thereof in an amount of about 28 to about 32% with respect to the total weight of the extended release layer, (b-2) an extended release agent in an amount of about 13 to about 17% with respect to the total weight of the extended release layer, and (a-3) a binder, (a-4) a lubricant, and (a-5) an excipient in an amount of about 47 to about 51% with respect to the total weight of the extended release layer.

In one embodiment of the present disclosure, in the pharmaceutical formulation, a weight ratio of the disintegrant to the binder contained in the immediate release layer may be about 1:2 to about 10:1. The weight ratio may be about 1:1 to 10:1, 1:2 to 5:1, or 1:1 to 5:1.

In one embodiment of the present disclosure, in the pharmaceutical formulation, a weight ratio of the extended release agent to the binder contained in the extended release layer may be about 1:60 to about 10:8. The weight ratio may be about 1:30 to 10:8, 1:60 to 5:8, or 1:30 to 5:8.

In one embodiment of the present disclosure, in the pharmaceutical formulation, a weight ratio of the (−)-cibenzoline or the pharmaceutically acceptable salt thereof to the disintegrant contained in the immediate release layer may be about 6:1 to about 50:1. The weight ratio may be about 12:1 to 50:1, 6:1 to 25:1, or 12:1 to 25:1.

In one embodiment of the present disclosure, in the pharmaceutical formulation, a weight ratio of the (−)-cibenzoline or the pharmaceutically acceptable salt thereof to the extended release agent contained in the extended release layer may be about 1:1 to about 4:1. The weight ratio may be about 2:1 to 4:1, 1:1 to 2:1, or 2:1 to 1:2.

In one embodiment of the present disclosure, in the pharmaceutical formulation, a weight ratio of the (−)-cibenzoline or the pharmaceutically acceptable salt thereof to the binder contained in the immediate release layer may be about 15:1 to about 100:1. The weight ratio may be about 30:1 to 100:1, 15:1 to 50:1, or 30:1 to 50:1.

In one embodiment of the present disclosure, in the pharmaceutical formulation, a weight ratio of the (−)-cibenzoline or the pharmaceutically acceptable salt thereof to the binder contained in the extended release layer may be about 2:1 to about 40:1. The weight ratio may be about 4:1 to 40:1, 2:1 to 20:1, or 4:1 to 20:1.

The present disclosure provides a pharmaceutical formulation for treating hypertrophic cardiomyopathy comprising the pharmaceutical formulation.

The present disclosure provides a kit comprising the pharmaceutical formulation and instructions that instruct a patient to administer the pharmaceutical formulation once a day.

Advantageous Effects

The pharmaceutical formulation including the immediate release layer and the extended release layer according to the present disclosure has a biphasic dissolution profile, such that it is possible to quickly reach an effective plasma concentration of S(−)-cibenzoline at the early stage, and the effective plasma concentration may be continuously maintained at the late stage. Therefore, the medicinal effect of S(−)-cibenzoline may be maintained only by an administration of a single formulation once a day.

DESCRIPTION OF DRAWINGS

FIG. 1 is a graph showing dissolution rates at pH 6.8, pH 1.2, and pH 4.5 of an extended release formulation of Example 1 of the present disclosure.

FIG. 2 is a graph showing dissolution rates at pH 6.8, pH 1.2, and pH 4.5 of an extended release formulation of Example 2 of the present disclosure.

FIG. 3 is a graph showing dissolution rates at pH 6.8, pH 1.2, and pH 4.5 of an extended release formulation of Example 3 of the present disclosure.

BEST MODE

In order to more easily understand the present disclosure, the terms used in the present disclosure are defined below.

The term "about" in the present disclosure is meant to include a range in which objects and effects of the present disclosure are exhibited. For example, in a case where an extended release agent is contained in an amount of about 5 to about 30% with respect to the total weight of an extended release layer, it may be interpreted to a range that may be extended to a range in which objects and effects of the present disclosure are exhibited by those skilled in the art by known techniques as well as a range of 5 to 30%.

Cibenzoline or Pharmaceutically Acceptable Salt Thereof

[Chemical Formula 1]

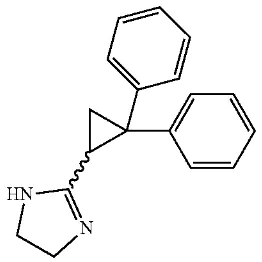

Cibenzoline (cifenline, 2-(2,2-diphenylcyclopropyl)-4,5-dihydro-1H-imidazole, 53267-01-9 (CAS number)) is a compound having a structure of Chemical Formula 1, and is a drug used as an antiarrhythmic agent which is a Group 1 sodium channel blocker. In addition, the effects of cibenzoline as a calcium channel blocker and a potassium channel blocker are also known.

The cibenzoline exists as two types of enantiomers such as S(−)-cibenzoline and R(+)-cibenzoline, and currently commercially available cibenzoline is a composition in which S(−)-cibenzoline and R(+)-cibenzoline are mixed in 1:1 (racemic mixture: 50:50 mixture of enantiomers). In the present disclosure, S(−)-cibenzoline is used as the cibenzoline.

The S(−)-cibenzoline of the present disclosure may contain not only a cibenzoline free salt but also a chloride thereof, and the cibenzoline may be not only a pharmaceutically acceptable salt or all hydrates and solvates. In one embodiment, the hydrate or solvate may be a crystallized or recrystallized solvate (in particular, a hydrate) obtained after dissolving the cibenzoline in a water-miscible solvent such as methanol, ethanol, acetone, or 1,4-dioxane, and then adding a free acid or a free base. In addition, stoichiometric solvates including various amounts of water-containing hydrates that may be prepared by a method such as lyophilization may also be included.

The chloride of the cibenzoline includes both an inorganic acid salt and an organic acid salt, and examples thereof include, but are not limited to, hydrochloride, sulfate, nitrate, phosphate, acetate, trifluoroacetate, benzenesulfonate, succinate, tartrate, maleate, citrate, and the like.

The cibenzoline may be formulated for administration to a patient, and contains one or more physiologically acceptable carriers or excipients. The carrier may be compatible with other components of the formulation and is not harmful to a recipient, and the drug may be formulated for oral, intravenous, or rectal administration. As an example of the formulation, the drug may be formulated into general forms such as a tablet, a capsule, and a syrup, but the present disclosure is not limited thereto.

Dosage

A suitable dosage of the pharmaceutical formulation of the present disclosure may be selected by various ways depending on factors such as a formulation method, a manner of administration, and an age, a weight, a gender, a pathological state, a food, an administration time, a route of administration, an excretion rate, and response sensitivity of a patient.

In one embodiment of the present disclosure, a once-daily dosage of the pharmaceutical formulation of the present disclosure may be about 150 mg to about 450 mg, about 150 mg to about 400 mg, or about 200 mg to about 400 mg, but is not limited thereto.

In addition, in one embodiment of the present disclosure, the once-daily dosage of the pharmaceutical formulation of the present disclosure may be 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, or 450 mg, but is not limited thereto.

Pharmaceutical Formulation

The pharmaceutical formulation of the present disclosure includes an immediate release layer (IR layer) and an extended release layer (ER layer). The immediate release layer refers to a formulation in which S(−)-cibenzoline or a pharmaceutically acceptable salt thereof is released relatively first to a living body as compared to the extended release layer, but is not limited to this configuration.

In one embodiment of the present disclosure, a formulation of each of the immediate release layer and the extended release layer may be a multiparticulate formulation, a matrix formulation, a sphere(s) formulation, or a double-layer (bilayer) tablet, but is not limited thereto.

In one embodiment of the present disclosure, the pharmaceutical formulation may comprise pellets containing S(−)-cibenzoline or a pharmaceutically acceptable salt thereof, drug-coated spheres containing cibenzoline or a pharmaceutically acceptable salt thereof, or at least two populations of layers containing cibenzoline or a pharmaceutically acceptable salt thereof. The first population of the pharmaceutical formulation immediately releases the drug in the upper gastrointestinal tract, and the second population of the pharmaceutical formulation releases the drug in the lower portion of the gastrointestinal tract. In one embodiment of the present disclosure, the second population may be coated by a pH dependent coating or a time dependent coating to delay the second release of the drug to a desired location in the gastrointestinal tract.

In one embodiment of the present disclosure, a weight ratio of the S(−)-cibenzoline or the pharmaceutically acceptable salt thereof contained in the immediate release layer:the cibenzoline or the pharmaceutically acceptable salt thereof contained in the extended release layer in the formulation may be about 1:4 to about 1:1, about 1:3 to about 1:1, about 3:7 to about 1:1, about 1:2 to about 1:1, about 7:13 to about 1:1, about 2:3 to about 1:1, about 9:11 to about 1:1, about 1:4 to 9:11, about 1:3 to about 9:11, about 3:7 to about 9:11, about 7:13 to about 9:11, about 2:3 to about 9:11, about 1:4 to 2:3, about 1:3 to about 2:3, about 3:7 to about 2:3, about 7:13 to about 2:3, about 1:4 to 7:13, about 1:3 to about 7:13, about 3:7 to about 7:13, about 1:4 to 3:7, about 1:3 to about 3:7, or about 1:4 to about 1:3.

When the weight ratio of the S(−)-cibenzoline or the pharmaceutically acceptable salt thereof contained in the immediate release layer:the cibenzoline or the pharmaceutically acceptable salt thereof contained in the extended release layer is less than about 1:4, it is difficult to obtain an effective effect immediately after administration of the drug, and when the weight ratio of the S(−)-cibenzoline or the pharmaceutically acceptable salt thereof contained in the immediate release layer:the cibenzoline or the pharmaceutically acceptable salt thereof contained in the extended release layer exceeds about 1:1, it is difficult to obtain an appropriate extended release effect because the amount thereof in the extended release layer is reduced.

Extended Release Layer

In one embodiment of the present disclosure, the extended release layer contains an extended release agent in order to have an extended release effect of the S(−)-cibenzoline or the pharmaceutically acceptable salt thereof.

In one embodiment of the present disclosure, the extended release agent is used to continuously maintain the drug for a certain period of time after reaching a therapeutic plasma concentration while being slowly released over a longer period of time than a drug in a general formulation.

In one embodiment of the present disclosure, the extended release agent may have a viscosity of about 1,500 to about 200,000 centipoise (cps), about 1,550 to about 200,000, about 1,600 to about 200,000 centipoise (cps), about 1,500 to about 180,000 centipoise (cps), about 1,550 to about 180,000, about 1,600 to about 180,000 centipoise (cps), about 1,500 to about 10,000 centipoise (cps), about 1,550 to about 150,000, or about 1,600 to about 150,000 centipoise (cps). When the viscosity is lower than about 1,500 centipoise or higher than about 200,000 centipoise, it may be difficult to achieve a preferred dissolution pattern according to the pharmacokinetic behavior of the S(−)-cibenzoline or the pharmaceutically acceptable salt thereof.

In one embodiment of the present disclosure, as the extended release agent, one or a mixture of two or more selected from an ionic agent, a swelling agent, and a hydrophobic agent is used.

In one embodiment of the present disclosure, the ionic agent refers to a pharmaceutically acceptable agent that controls the release of the drug through an ionic bond with the drug, and includes one or more selected from sodium carboxymethyl cellulose, carbomer, and sodium alginate.

In one embodiment of the present disclosure, the swelling agent refers to a pharmaceutically acceptable agent that swells instantaneously in an aqueous solution and controls the release of the drug through a reduction of pores, and includes one or more selected from hydroxyethyl cellulose and a salt or derivative thereof, hydroxypropyl methylcellulose and a salt or derivative thereof, polyethylene oxide and a salt or derivative thereof, and carrageenan.

In one embodiment of the present disclosure, the hydrophobic agent refers to a pharmaceutically acceptable agent that is not dissolved in an aqueous solution and controls the release of the drug through pore blocking, and includes one or more selected from polyvinyl acetate, glyceryl behenate, hydrogenated castor oil, hydrogenated vegetable oil, and stearic acid.

In one embodiment of the present disclosure, the extended release agent includes one or more selected from hydroxyethyl cellulose, hydroxypropyl methylcellulose, and a salt or derivative thereof, polyethylene oxide and a salt or derivative thereof, sodium carboxymethyl cellulose, carbomer, and polyvinyl acetate.

In one embodiment of the present disclosure, the amount of the extended release agent is about 5 to about 30 parts by weight, about 6 to about 30 parts by weight, or about 7 to about 30 parts by weight, with respect to 100 parts by weight of the extended release layer. When the amount of the extended release agent is about 5 to about 30 parts by weight, the drug release control may be excellent, and it is possible to reach an optimal plasma concentration at an appropriate release rate of the cibenzoline or the pharmaceutically acceptable salt thereof. When the amount of the extended release agent exceeds about 30 parts by weight, the release of the drug at the early stage is slow, the drug is not dissolved 100% within about 12 hours, and the size of the drug is increased. When the amount of the extended release agent is less than about 5 parts by weight, the release of the drug at the early stage is fast, and the entire drug is released in advance within about 12 hours.

Immediate Release Layer

In one embodiment of the present disclosure, the immediate release layer is a formulation containing a disintegrant or a formulation containing no extended release agent in order to have an immediate release effect of the S(−)-cibenzoline or the pharmaceutically acceptable salt thereof.

In one embodiment of the present disclosure, the disintegrant is used to absorb moisture and promote disintegration of the formulation in order to improve dissolution.

In one embodiment of the present disclosure, the disintegrant includes one or more selected from carboxymethylcellulose calcium, pregelatinized starch, sodium starch glycolate, crospovidone (polyplasdone), croscarmellose sodium, low-substituted hydroxypropylcellulose, alginic acid, powdered cellulose, starch, sodium alginate, and a mixture thereof.

In one embodiment of the present disclosure, the amount of the disintegrant is about 1 to about 10 parts by weight or about 1 to about 5 parts by weight with respect to 100 parts by weight of the immediate release layer. When the content of the disintegrant is too low, the dissolution is not improved. In addition, when the content of the disintegrant is too excessive, the hardness of the final formulation is adversely affected and the formulation is easily broken.

Excipient

In one embodiment of the present disclosure, an excipient may be additionally contained in order to secure stability for long-term storage and to have continuous extended release effect. In the present disclosure, the excipient refers to a diluent, a binder, a lubricant, or the like.

In one embodiment of the present disclosure, for example, the diluent may be selected from the group consisting of lactose, lactose monohydrate, dextrin, mannitol, sorbitol, starch, microcrystalline cellulose, calcium hydrogen phosphate, anhydrous calcium hydrogen phosphate, calcium carbonate, saccharides, and a mixture thereof.

In one embodiment of the present disclosure, the binder serves to increase a binding force of the formulation. The binder may be selected from the group consisting of polyvinylpyrrolidone, copovidone, gelatin, sucrose, methyl cellulose, ethyl cellulose, and a mixture thereof.

In one embodiment of the present disclosure, the lubricant improves mobility of powder and granule materials to increase fillability into a die located at a lower portion of a tablet machine and to reduce friction between the powder and granule materials and between the powder and granule materials and a punch, which is located at an upper portion of the tablet machine, and the die, thereby facilitating compression and release of tablets. The lubricant may be, for example, light anhydrous silicic acid, colloidal silicon dioxide, talc, stearic acid, magnesium stearate, and a mixture thereof.

Dissolution Test

A dissolution test is a test according to Dissolution method II (paddle method) in United States Pharmacopeia (or Korean Pharmacopeia).

Biphasic Profile

In one embodiment of the present disclosure, the biphasic dissolution profile of the formulation may include an immediate release phase (or instant release phase) that is a first phase and an extended release phase that is a second phase (or delayed release phase).

The first phase is a part of the dissolution profile obtained within 0 to about 30 minutes in an in-vitro dissolution test, and 30 to 50% of the total weight of the S(−)-cibenzoline or the pharmaceutically acceptable salt thereof is released within about 30 minutes from the first phase. The "within about 30 minutes" designates a point in time when a certain amount of time has elapsed after administration, and includes within about 10 minutes, within about 15 minutes, or within about 20 minutes.

The second phase is a part of the dissolution profile after about 30 minutes measured in the in-vitro dissolution test. The "after about 30 minutes" designates a point in time when a certain amount of time has elapsed after administration, and includes after about 10 minutes, after about 15 minutes, or after about 20 minutes.

In one embodiment of the present disclosure, in the formulation, about 50 to about 90% or about 50 to 80% of the total weight of the S(−)-cibenzoline or the pharmaceutically acceptable salt thereof is released from the second phase.

"Cmax", "Cmin", "Tmax", "Tmin", "AUC"

"Cmax", "Cmin", "Tmax", and "Tmin" in the present disclosure are terms used for pharmacokinetic analysis of a drug concentration over time. Cmax is a term representing a maximum (or peak) plasma concentration achieved by a drug in a particular compartment or a test area of a body after administration of the drug and before administration of a second dose of the drug. Cmax is a term opposite to Cmin that is a minimum (or trough) concentration achieved by the drug after administration. Tmax is a term used in pharmacokinetics to describe the time at which Cmax is observed, and Tmin is a term used in pharmacokinetics to describe the time at which Cmin is observed after administration of the drug and before administration of the second dose of the drug.

In one embodiment of the present disclosure, the Cmax of the formulation is about 280 to about 420 ng/mL when the formulation is administered as a single dose of 200 mg once a day. In addition, the Cmax of the formulation is about 430 to about 570 ng/mL when the formulation is administered as a single dose of 300 mg once a day. As for the Cmax value, an appropriate numerical value representing the effect in pharmacodynamic analysis may be increased as the dosage and the number of administrations are increased. In one embodiment of the present disclosure, the Cmax of the formulation satisfies about 1 to about 3 hours (that is, Tmax) after administration of the formulation.

"AUC" in the present disclosure refers to an area under a curve (mathematically known as a definite integral) in a pharmacokinetic plot of a drug concentration over time.

In one embodiment of the present disclosure, the formulation satisfies an area under a target curve (hereinafter, referred to as an area under the curve (AUC)) of about 1,890 to about 2,830 ng·hr/mL over 24 hours when the formulation is administered as a single dose of 200 mg once a day. In addition, the AUC of the formulation is about 3,390 to about 4,330 ng·hr/mL when the formulation is administered as a single dose of 300 mg once a day. As for the AUC value, an appropriate numerical value representing the effect in pharmacodynamic analysis may be increased as the dosage and the number of administrations are increased.

In one embodiment of the present disclosure, a plasma concentration [C] of the S(−)-cibenzoline in the formulation is about 150 ng/mL or more for about 6 hours to about 18 hours out of 24 hours. In addition, the plasma concentration [C] of the S(−)-cibenzoline is about 100 ng/mL or more for 24 hours. In one embodiment of the present disclosure, a minimum plasma concentration within the above time range appears even when the formulation is administered once a day.

Pharmaceutical Composition

A minimum effective plasma concentration is achieved within about 0.25 to about 1 hour after the pharmaceutical formulation of the present disclosure is administered to a patient. In one embodiment of the present disclosure, a minimum effective plasma concentration of about 150 to about 800 ng/mL is achieved in the immediate release layer of the pharmaceutical formulation.

Hypertrophic Cardiomyopathy (HCM)

Hypertrophic cardiomyopathy includes a group of highly expressed, monogenic, autosomal dominant myocardial diseases, and is caused by one or more of over 1,000 known point mutations in any one of structural protein genes contributing to sarcomere that is a functional unit of myocardium. Hypertrophic cardiomyopathy was initially considered to be a very rare disease. However, currently, it has been found that hypertrophic cardiomyopathy is the most common disease that is caused at a high frequency of 1 in 500 births and causes sudden death especially at a young age, and is inherited in an autosomal dominant manner. Hypertrophic cardiomyopathy is often discovered incidentally while performing electrocardiogram and echocardiography for health check-ups in young adults, and then is followed up.

Hemodynamic or symptomatic hypertrophic cardiomyopathy may be divided into obstructive and non-obstructive types. The obstructive type may be divided into subvalvular obstruction and ventricular central obstruction, and the delayed obstructive type refers to a case where there is no pressure gradient at rest, but a pressure gradient of 30 mmHg or more occurs during provocation.

Clinical symptoms for patients with hypertrophic cardiomyopathy are dyspnea on exertion, and include a systemic arterial thromboembolic disease such as apoplexy, acute pulmonary edema, atrial fibrillation, intolertance of hypovolemia or hypervolemia, and fainting. Recently, sudden cardiac death (SCD) has also been identified as a major symptom of hypertrophic cardiomyopathy.

Kit

A kit refers to a packaged product containing components for administering the S(−)-cibenzoline of the present disclosure or the pharmaceutically acceptable salt thereof for treating hypertrophic cardiomyopathy. The kit includes a container or box that holds the components of the kit. The box or container is accompanied by a protocol or label approved by the Food and Drug Administration. The box or container holds the components of the present disclosure contained in a plastic, polyethylene, polypropylene, ethylene, or propylene container. The container may be a tube or bottle with a lid. The kit also includes instructions for administering the S(−)-cibenzoline of the present disclosure or the pharmaceutically acceptable salt thereof.

Hereinafter, the present disclosure will be described in detail with reference to the following Examples. However, the following Examples are only examples for describing the present disclosure, and the scope of the present disclosure is not limited thereto.

Examples 1 to 3: Preparation of Pharmaceutical Formulation According to Content of S(−)-Cibenzoline Succinate Double layer tablets were prepared according to a content of S(−)-cibenzoline succinate as shown in the components and contents of Table 1. The total contents of S(−)-cibenzoline succinate were set to 200 mg in Example 1, 300 mg in Example 2, and 400 mg in Example 3, respectively. A detailed preparation process is as follows.

Preparation Processes of Examples 1 and 2

<Step 1> Preparation of Immediate Release Layer

Hydroxypropylcellulose is dissolved in purified water at room temperature to prepare a binding solution. S(−)-cibenzoline succinate, microcrystalline cellulose, and lactose monohydrate sieved through a 30-mesh sieve are mixed in a high-speed mixer (HSM) (Pilotmix 150T, Huttlin) for about 5 minutes. The prepared binding solution is added to the mixture and granules are prepared in the high-speed mixer for about 5 minutes. The prepared wet granules are subjected to wet milling, and then the wet milled granules are moved to a fluid bed granulator (FBG) (Pilotlab L, Huttlin) to be dried. The dried granules are sized by being passed through a cone mill. Calcium carboxymethyl cellulose and microcrystalline cellulose sieved through a 30-mesh sieve are mixed with the sized granules for about 22 minutes. An immediate release layer is prepared by lubricating magnesium stearate sieved through a 40-mesh sieve in the prepared mixture for about 5 minutes.

<Step 2> Preparation of Extended Release Layer

Hydroxypropylcellulose is dissolved in purified water at room temperature to prepare a binding solution. S(−)-cibenzoline succinate, microcrystalline cellulose, and lactose monohydrate sieved through a 30-mesh sieve are mixed in a high-speed mixer (HSM) (Pilotmix 150T, Huttlin) for about 5 minutes. The prepared binding solution is added to the mixture and granules are prepared in the high-speed mixer for about 5 minutes. The prepared wet granules are subjected to wet milling, and then the wet milled granules are moved to a fluid bed granulator (FBG) (Pilotlab L, Huttlin) to be dried. The dried granules are sized by being passed through a cone mill. Hydroxypropyl methylcellulose, hydroxypropylcellulose, and microcrystalline cellulose sieved through a 30-mesh sieve are mixed with the sized granules for about 17 minutes. An extended release layer is prepared by lubricating magnesium stearate sieved through a 40-mesh sieve in the prepared mixture for about 5 minutes.

<Step 3> Preparation of Double Layer Tablet

The prepared granules for the immediate release layer and the extended release layer were prepared into a double layer tablet including the respective layers using a double layer tablet machine (double layer tablet compression machine, Kilian). A film coating was performed using the prepared Opadry.

Preparation Process of Example 3

<Step 1> Preparation of Immediate Release Layer

S(−)-cibenzoline succinate, microcrystalline cellulose, hydroxypropylcellulose, and lactose monohydrate sieved through a 30-mesh sieve at room temperature are mixed in a high-speed mixer (HSM) (Pilotmix 150T, Huttlin) for about 10 minutes. Purified water is added to the mixture, and mixing is performed in the high-speed mixer for about 5 minutes, thereby preparing granules. The prepared wet granules are subjected to wet milling, and then the wet milled granules are moved to a fluid bed granulator (FBG) (Pilotlab L, Huttlin) to be dried. The dried granules are sized by being passed through a cone mill. Colloidal silicon dioxide sieved through a 30-mesh sieve is mixed with the sized granules for about 17 minutes. An immediate release layer is prepared by lubricating magnesium stearate sieved through a 40-mesh sieve in the prepared mixture for about 5 minutes.

<Step 2> Preparation of Extended Release Layer

S(−)-cibenzoline succinate, microcrystalline cellulose, hydroxypropylcellulose, and lactose monohydrate sieved through a 30-mesh sieve at room temperature are mixed in a high-speed mixer (HSM) (Pilotmix 150T, Huttlin) for about 10 minutes. Purified water is added to the mixture, and mixing is performed in the high-speed mixer for about 5 minutes, thereby preparing granules. The prepared wet granules are subjected to wet milling, and then the wet milled granules are moved to a fluid bed granulator (FBG) (Pilotlab L, Huttlin) to be dried. The dried granules are sized by being passed through a cone mill. Hydroxypropyl methylcellulose, hydroxypropylcellulose, and colloidal silicon dioxide sieved through a 30-mesh sieve are mixed with the sized granules for about 17 minutes. An extended release layer is prepared by lubricating magnesium stearate sieved through a 40-mesh sieve in the prepared mixture for about 5 minutes.

<Step 3> Preparation of Double Layer Tablet

The prepared granules for the immediate release layer and the extended release layer were prepared into a double layer tablet including the respective layers using a double layer tablet machine (double layer tablet compression machine, Kilian). A film coating was performed using the prepared Opadry.

TABLE 1

| Classification | | | Example 1 (S(−)-cibenzoline succinate 200 mg) | Example 2 (S(−)-cibenzoline succinate 300 mg) | Example 3 (S(−)-cibenzoline succinate 400 mg) |
|---|---|---|---|---|---|
| Immediate release layer | Main component | S(−)-cibenzoline succinate | 70.000 mg (40%) | 105.000 mg (40%) | 100.000 mg (26.32%) |
| | Diluent | Micro-crystalline cellulose | 24.500 mg (14%) | 36.750 mg (14%) | 129.000 mg (33.95%) |
| | Diluent | Lactose mono-hydrate | 24.500 mg (14%) | 36.750 mg (14%) | 129.000 mg (33.95%) |
| | Binder | Hydro-xypropyl-cellulose | 1.680 mg (0.96%) | 2.520 mg (0.96%) | 15.000 mg (3.95%) |
| | Dis-integrant | Carbo-xymethyl-cellulose calcium | 4.200 mg (2.40%) | 6.300 mg (2.40%) | N/A |
| | Diluent | Micro-crystalline cellulose | 48.020 mg (27.44%) | 72.030 mg (27.44%) | N/A |
| | Lubricant | Magnesium stearate | 2.100 mg (1.20%) | 3.150 mg (1.20%) | 5.500 mg (1.45%) |
| | Lubricant | Colloidal silicon dioxide | N/A | N/A | 1.500 mg (0.39%) |
| | Total | | 175.000 mg (100%) | 262.500 mg (100%) | 380.000 mg (100%) |
| Extended release layer | Main component | S(−)-cibenzoline succinate | 130.000 mg (30.59%) | 195.000 mg (30.59%) | 300.000 mg (36.59%) |
| | Diluent | Micro-crystalline cellulose | 45.500 mg (10.71%) | 68.250 mg (10.71%) | 196.000 mg (23.90%) |
| | Diluent | Lactose mono-hydrate | 45.500 mg (10.71%) | 68.250 mg (10.71%) | 196.000 mg (23.90%) |
| | Binder | Hydro-xypropyl-cellulose | 3.120 mg (0.73%) | 4.680 mg (0.73%) | 33.000 mg (4.02%) |
| | Extended release agent | Hydro-xypropyl methyl-cellulose (Methocel K4M DC2) | 63.750 mg (15%) | 95.625 mg (15%) | 78.000 mg (9.51%) |
| | Binder | Hydro-xypropyl-cellulose | 21.250 mg (5%) | 31.875 mg (5%) | N/A |
| | Diluent | Micro-crystalline cellulose | 110.580 mg (26.02%) | 165.870 mg (26.02%) | N/A |
| | Lubricant | Magnesium stearate | 5.300 mg (1.25%) | 7.950 mg (1.25%) | 13.000 mg (1.59%) |
| | Lubricant | Colloidal silicon dioxide | N/A | N/A | 4.000 mg (0.49%) |
| | Total | | 425.000 mg (100%) | 637.500 mg (100%) | 820.000 mg (100%) |
| Coating layer | Coating agent | Opadry | 18.000 mg | 27.000 mg | 36.000 mg |
| Total | | | 618.000 mg | 927.000 mg | 1,236.000 mg |

The content (w %) in the table is parts by weight.

Examples 4 to 7: Preparation of Formulation According to Content (w %) of Extended Release Agent in Extended Release Layer In order to confirm the effect of the content of the extended release agent in the composition of the extended release layer of Example 1 in Table 1, formulations of Examples 4 to 6 were prepared by adjusting the content of hydroxypropyl methylcellulose as the extended release agent. Formulations of Examples 6 to 9 were prepared by adjusting the content of hydroxypropyl methylcellulose as the extended release agent in the composition of the extended release layer of Example 3. The adjusted weight of the extended release agent and the adjusted content (w %) of the extended release agent in the extended release layer are as shown in Table 2.

TABLE 2

| | Example 1 | Example 2 | Example 3 | Example 4 | Example 5 | Example 6 | Example 7 | Example 8 | Example 9 |
|---|---|---|---|---|---|---|---|---|---|
| Ratio of extended release layer in entire tablet (w %) | 68.8 | | 66.3 | | 68.8 | | | 66.3 | |
| Content of extended release agent in extended release layer (w %) | 15 | 15 | 9.5 | 5 | 7.5 | 30 | 5 | 7.5 | 30 |
| Weight of extended release layer (mg) | 425.000 | 637.500 | 820.000 | 425.000 | 425.000 | 425.000 | 820.000 | 820.000 | 820.000 |
| Weight of hydroxypropyl methylcellulose (mg) | 63.750 | 95.625 | 78.000 | 21.250 | 31.875 | 127.500 | 41.000 | 61.500 | 246.000 |

Examples 10 to 15 and Comparative Examples 1 to 4: Preparation of Formulation According to Weight Ratio of S(−)-Cibenzoline Succinate Contained in Immediate Release Layer and S(−)-Cibenzoline Succinate Contained in Extended Release Layer Based on the composition of Example 1 shown in Table 1, in order to confirm the effect according to the ratio between S(−)-cibenzoline succinates contained in the immediate release layer and the extended release layer, formulations of Examples 10 to 15 and Comparative Examples 1 to 4 were prepared by changing the weight ratio of the S(−)-cibenzoline succinate contained in the immediate release layer and the S(−)-cibenzoline succinate contained in the extended release layer. The changed ratios are shown in Table 3.

TABLE 3

| | Comparative Example 1 | Comparative Example 2 | Example 10 | Example 11 | Example 12 | Example 1 | Example 13 | Example 14 | Example 15 | Comparative Example 3 | Comparative Example 4 |
|---|---|---|---|---|---|---|---|---|---|---|---|
| Weight ratio of S(−)-cibenzoline succinate contained in immediate release layer to S(−)-cibenzoline succinate contained in extended release layer | Extended release formulation | 1:9 | 1:4 | 1:3 | 3:7 | 7:13 | 2:3 | 9:11 | 1:1 | 11:9 | Immediate release formulation |
| Weight of S(−)-cibenzoline succinate contained in immediate release layer (mg) | 0 | 20 | 40 | 50 | 60 | 70 | 80 | 90 | 100 | 110 | 200 |
| Weight of S(−)-cibenzoline succinate contained in extended release layer (mg) | 200 | 180 | 160 | 150 | 140 | 130 | 120 | 110 | 100 | 90 | 0 |

Examples 16 and 17: Preparation of Formulation According to Viscosity of Hydroxypropyl Methylcellulose Based on the composition of Example 1 shown in Table 1, formulations of Examples 16 and 17 were prepared by changing the viscosity of the hydroxypropyl methylcellulose as the extended release agent contained in the extended release layer from 2,700 to 5,040 cps. The changed viscosities are shown in Table 4.

TABLE 4

| | Example 1 (Methocel K4M DC2) | Example 16 (Methocel K15M DC) | Example 17 (Methocel K100M) |
|---|---|---|---|
| Viscosity of hydroxypropyl methylcellulose (cps) | 2,700 to 5,040 | 13,500 to 25,200 | 100,000 to 140,000 |

Experimental Example 1: In-Vitro Dissolution Test [Dissolution Test]

The dissolution test was performed as follows according to United States Pharmacopeia (USP) test method (see, <711> dissolution, apparatus 2) using a dissolution device (EV06300, DISTEK).

<Dissolution Test Conditions>

As the dissolution solution, one or more of the following four solutions are used.

1) Phosphate buffer solution 900 mL (pH 6.8)
2) 0.1 N HCl aqueous solution 900 mL (pH 1.2)
3) Acetate buffer solution 900 mL (pH 4.5)
4) Distilled water 900 mL Dissolution temperature: 37° C.

Speed of revolution of paddle: 50 rpm

<High Performance Liquid Chromatography (HPLC) Conditions>

Column: Inertsil ODS-3V (4.6×150 mm, 5 μm)

Mobile phase: Phosphate buffer solution (containing sodium 1-octanesulfonate):acetonitrile=650:350 (v/v)

Detector: Ultraviolet (UV) detector

Flow rate: 1.5 ml/min

Injection amount: 5 μl

Under the dissolution test conditions, the dissolution solution was acquired at 15 minutes, 30 minutes, 60 minutes, 120 minutes, 180 minutes, 300 minutes, 360 minutes, 480 minutes, 600 minutes, and 720 minutes, and the acquired dissolution solution was filtered to obtain a test solution.

Additionally, 55.5 mg of the S(−)-cibenzoline succinate was precisely weighed and placed in a 50 mL flask, and the S(−)-cibenzoline succinate was dissolved with a dissolution solution and then was marked. This solution was appropriately diluted according to a test solution concentration and used as a standard solution. In addition, the sample solution and the standard solution were analyzed under the HPLC analysis conditions.

Experimental Example 1-A: Dissolution Test for Examples 1 to 9 According to Content (w %) of Extended Release Agent in Extended Release Layer As a result of the dissolution test according to the content (w %) of the extended release agent in the extended release layer shown in Table 2, in all Examples 1 to 9, the cumulative dissolution amounts were about 30 to about 50% within about 30 minutes, about 60% or more and about 75% or less within about 3 hours, and about 90% or more within about 12 hours. In addition, the cumulative dissolution amounts were about 30 to about 50% within about 15 minutes, about 55% or more and about 75% or less within about 3 hours, and about 80% or more within about 12 hours.

Experimental Example 1-B: Dissolution Test for Examples 11 to 17 and Comparative Examples 1 to 4 According to Weight Ratio of S(−)-Cibenzoline Succinate Contained in Immediate Release Layer and S(−)-Cibenzoline Succinate Contained in Extended Release Layer As shown in Table 5, the cumulative dissolution amounts of Examples 11 to 17 of Tables 3 and 4 were about 30 to about 50% within about 30 minutes, about 60% or more and about 75% or less within about 3 hours, and about 90% or more within about 12 hours, and the cumulative dissolution amounts were about 30 to about 50% within about 15 minutes, about 55% or more and about 75% or less within about 3 hours, and about 80% or more within about 12 hours. On the other hand, the formulation of Comparative Example 1 is a single extended release formulation and the formulation of Comparative Example 2 is a formulation in which the content of the S(−)-cibenzoline succinate contained in the extended release layer is about 90% (ratio of 1/9) with respect to the entire tablet, and in the cases of these formulations, the cumulative dissolution amount is less than about 30% within about 30 minutes, and thus, it is difficult to exert the medicinal effect of the formulation after initial administration. The formulation of Comparative Example 3 is a formulation in which the content of the S(−)-cibenzoline succinate contained in the extended release layer is about 45% (ratio of 9/20) with respect to the entire tablet, the formulation of Comparative Example 4 is a single immediate release formulation, and in the cases of these formulations, the cumulative dissolution amount exceeds about 80% within about 6 hours, and thus, it is difficult to obtain the extended release effect.

TABLE 5

| | Dissolution characteristics | Evaluation |
|---|---|---|
| Examples 11 to 17 | Cumulative dissolution amounts are about 30 to about 50% within about 30 minutes, about 60% or more and about 75% or less within about 3 hours, and about 90% or more within about 12 hours, and cumulative dissolution amounts are about 30 to about 50% within about 15 minutes, about 55% or more and about 75% or less within about 3 hours, and about 80% or more within about 12 hours | It is estimated to exert appropriate medicinal effect |
| Comparative Examples 1 and 2 | Cumulative dissolution amount is less than about 30% within about 30 minutes | It is estimated that it will be difficult to exert medicinal effect after initial administration |
| Comparative Examples 3 and 4 | Cumulative dissolution amount exceeds about 80% within about 6 hours | It is estimated that the release rate of the drug is fast and it |

TABLE 5-continued

| Dissolution characteristics | Evaluation |
|---|---|
| | will be difficult to exert extended release effect after initial administration |

Experimental Example 1-C: Cumulative Dissolution Amount (%) of Extended Release Formulation of S(−)-Cibenzoline Succinate According to Change in pH As shown in Table 6 and illustrated in FIGS. 1 to 3, it was confirmed that, depending on the pH environment of the digestive system of the living body, the cumulative dissolution amounts of Examples 1 to 3 were about 30 to about 50% within about 30 minutes, about 60% or more and about 75% or less within about 3 hours, and about 90% or more within about 12 hours, and the cumulative dissolution amounts were about 30 to about 50% within about 15 minutes, about 55% or more and about 75% or less within about 3 hours, and about 80% or more within about 12 hours. In addition, as illustrated in FIGS. 1 to 3, it was confirmed that the biphasic dissolution profile in which the slope of the dissolution profile was changed before and after 1 hour at the early stage was satisfied.

TABLE 6

| Classification | | 0.25 | 0.5 | 1 | 2 | 3 | 5 | 6 | 8 | 10 | 12 |
|---|---|---|---|---|---|---|---|---|---|---|---|
| Example 1 | pH 6.8 | 44 | 48 | — | 64 | 70 | 81 | 85 | 91 | 95 | 98 |
| 200 mg | pH 1.2 | 43 | 49 | 56 | 67 | 74 | 86 | 90 | 96 | 99 | 100 |
| (IR:ER = 35:65) | pH 4.5 | 43 | 48 | 55 | 64 | 71 | 82 | 86 | 94 | 98 | 101 |
| Example 2 | pH 6.8 | 44 | 51 | — | 58 | 63 | 72 | 75 | 81 | 86 | 90 |
| 300 mg | pH 1.2 | 39 | 43 | 50 | 59 | 66 | 77 | 81 | 88 | 93 | 99 |
| (IR:ER = 35:65) | pH 4.5 | 37 | 42 | 47 | 55 | 60 | 70 | 73 | 80 | 86 | 91 |
| Example 3 | pH 6.8 | 27 | 40 | 48 | 59 | 67 | 80 | 85 | 92 | 97 | 99 |
| 400 mg | pH 1.2 | 23 | 36 | 46 | 58 | 68 | 82 | 87 | 95 | 99 | 100 |
| (IR:ER = 25:75) | pH 4.5 | 29 | 37 | 46 | 56 | 64 | 77 | 82 | 90 | 96 | 100 |

"—" The value is not confirmed due to measurement error

Experimental Example 2: In-Vivo Pre-Clinical Test

In the in-vitro dissolution test of Experimental Example 1, the in-vivo pharmacokinetics of the extended release formulation of Example 1 in which the dissolution aspects under various pH conditions were confirmed by the following pre-clinical test.

As for the test method, each tablet of the formulation excluding the hydroxypropyl methylcellulose as the extended release agent of Example 1 and the formulation of Comparative Example 5 was orally administered to a beagle dog (male, n=6), blood was collected at a predetermined time, plasma was separated, and then, a concentration of the S(−)-cibenzoline succinate in the plasma of the beagle dog was measured. 1.5 mL of the blood was collected every 0.33, 0.66, 1, 1.5, 2, 2.5, 3, 4, 6, 8, 10, 12, 16, and 24 hours after administration. The amount of the S(−)-cibenzoline succinate in blood was analyzed by an LC-MS/MS analysis method, and pharmacokinetic parameters were analyzed using Phoenix WinNonlin® Ent-Version 8.1 program.

The time to reach maximum plasma concentration (tmax), the maximum plasma concentration (Cmax), the area under the plasma concentration-time curve up to 24 hours of quantitative time (AUC0-24h), the area under the plasma concentration-time curve from the onset of administration to the unlimited time (AUC0-inf), and the plasma half-life (t1/2) that were the analysis results of the test as shown in Table 7 were calculated.

TABLE 7

| Pharmacokinetic parameters | Example 1 | Comparative Example 5 |
|---|---|---|
| $T_{max}$ (h) | 2.0 (0.66-3.0) | 0.66 (0.33-1.50) |
| $C_{max}$ (ng/mL) | 2110.047 | 3160.389 |
| $AUC_{0-24\ h}$ (ng · h/mL) | 14179.932 | 13987.574 |
| $AUC_{0-inf}$ (ng · h/mL) | 14279.128 | 14094.982 |
| $T_{1/2}$ (h) | 2.928 | 3.132 |

As shown in Table 7, it was confirmed that in Example 1, the Cmax value was lowered by about 1.5 times and the Tmax value was increased by about three times relative to those in Comparative Example 5, and the extended release effect was obtained. It could be confirmed through this experiment that the time to reach maximum plasma concentration (tmax) was delayed, and thus, the in-vitro dissolution aspect and the in-vivo dissolution aspect were same as each other. Based on this experiment, the optimal effect was confirmed in the clinical test as a final goal of the present disclosure.

Experimental Example 3: Pharmacodynamic Analysis Confirmed in Healthy Patients of Examples 1 and 2 (Single Administration)

This study is a clinical trial for evaluating safety and tolerability for a day by orally administrating 200 mg or 300 mg of the S(−)-cibenzoline succinate extended release tablet formulation having the composition of each of Examples 1 and 2 once a day or orally administrating 150 mg of the racemic mixture (S-isomer:R-isomer=50:50) cibenzoline succinate having the composition of Comparative Example 5 three times a day, to healthy subjects. More specifically, the clinical test was conducted by administration as follows.

Cohort 1: Single oral administration of 200 mg of S(−)-cibenzoline succinate once a day Cohort 2: Single oral administration of 300 mg of S(−)-cibenzoline succinate once a day Cohort 3: Single oral administration of 150 mg of racemic mixture (S-isomer:R-isomer=50:50) cibenzoline succinate three times a day In this study, a total of 24 test subjects were randomly assigned at 1:1:1 to three cohorts and four stages of screening, treatment period 1, withdrawal period, and treatment period 2 were performed. A ratio of the administered group to the non-administered group (placebo) was assigned at 6:2.

As the main evaluation variables, the area under the plasma concentration-time curve (AUC), the maximum plasma concentration of the drug ($C_{max}$), the time to reach maximum plasma concentration ($t_{max}$), and the half-life of the maximum plasma concentration ($t_{1/2}$) were measured for blood pharmacokinetic analysis of dose escalation of S(−)-cibenzoline succinate in the healthy subjects.

When participating in the cohorts 1 and 2, pharmacokinetic blood collection was performed for 48 hours (within 60 minutes before taking the test drug, and every 30 minutes, 1 hour, 1 hour 30 minutes, 2 hours, 2 hours 30 minutes, 3 hours, 4 hours, 6 hours, 8 hours, 10 hours, 12 hours, 16 hours, 24 hours, 30 hours, 36 hours, and 48 hours after taking the test drug). When participating in the cohort 3, the pharmacokinetic blood collection was performed based on administration at 8 am before taking CT-G11 and every 30 minutes, 1 hour, 1 hour 30 minutes, 2 hours, 2 hours 30 minutes, 3 hours, 4 hours, and 8 hours after taking CT-G11 (performed before taking CT-G11 at 4 pm as the second dose), and was performed 30 minutes, 1 hour, 1 hour 30 minutes, 2 hours, 2 hours 30 minutes, 3 hours, 4 hours, and 8 hours, after the second administration of the test drug (performed before the third administration of the test drug). Blood collection was performed after 30 minutes, 1 hour, 1 hour 30 minutes, 2 hours, 2 hours 30 minutes, 3 hours, and 4 hours, respectively, after the third administration of the test drug.

As the plasma concentration of the S(−)-cibenzoline succinate, a plasma concentration of the S(−)-cibenzoline succinate was measured from the pre-treated blood samples using LC-MS. As shown in Table 8, it was confirmed that three formulations were shown to exert the pharmacodynamically equivalent medicinal effect, and the minimum effective plasma concentration of about 100 to 150 ng/mL or more was maintained, the minimum effective plasma concentration being confirmed through the previously performed beagle dog non-clinical (in-vivo) experiment, and thus, the effect of the drug was maintained in the patients for 24 hours.

TABLE 8

| Pharmacodynamic analysis | Cohort 1 200 mg of S(−)-cibenzoline succinate once a day | Cohort 2 300 mg of S(−)-cibenzoline succinate once a day | Cohort 3 150 mg of racemic mixture cibenzoline succinate three times a day |
|---|---|---|---|
| Cmax (ng/mL) | 328.6 | 478.0 | 193.2 |
| AUC24 (h*ng/mL) | 2674.1 | 4076.3 | 3610.3 |
| AUC (h*ng/mL) | 2742.7 | 4154.7 | 3689.4 |
| Tmax (h) | 2.0 | 1.8 | 9.5 |
| t1/2 (h) | 9.0 | 8.4 | 6.4 |
| Minimum effective plasma concentration (ng/mL) | 100 to 150 | 100 to 150 | 100 to 150 |

Experimental Example 4: Pharmacodynamic Analysis Confirmed in Healthy Patients of Examples 1 and 2 (Multiple Administration)

This study is a clinical trial for evaluating safety and tolerability by orally administrating 200 mg or 300 mg of the S(−)-cibenzoline succinate extended release tablet formulation having the composition of each of Examples 1 and 2 once a day or orally administrating 150 mg of the racemic mixture (S-isomer:R-isomer=50:50) cibenzoline succinate having the composition of Comparative Example 5 three times a day, to healthy subjects. More specifically, the clinical test was conducted by administration as follows.

Cohort 4: Multiple oral administration of 200 mg of S(−)-cibenzoline succinate once a day for 5 days Cohort 5: Multiple oral administration of 300 mg of S(−)-cibenzoline succinate once a day for 14 days Cohort 6: Multiple oral administration of 150 mg of racemic mixture (S-isomer:R-isomer=50:50) cibenzoline succinate three times a day for 14 days In this study, a total of 24 test subjects were randomly assigned at 1:1:1 to three cohorts and four stages of screening, treatment period 1, withdrawal period, and treatment period 2 were performed. A ratio of the administered group to the non-administered group (placebo) was assigned at 6:2.

As the main evaluation variables, the area under the plasma concentration-time curve (AUC), the maximum plasma concentration of the drug ($C_{max}$), the time to reach maximum plasma concentration ($t_{max}$), and the half-life of the maximum plasma concentration ($t_{1/2}$) were measured for blood pharmacokinetic analysis of dose escalation of S(−)-cibenzoline succinate in the healthy subjects.

When participating in the cohort 4, pharmacokinetic blood collection was performed for 6 days (within 60 minutes before taking the test drug on the 3rd and 4th days, within 60 minutes before taking the test drug on the 14th day, every 30 minutes, 1 hour, 1 hour 30 minutes, 2 hours, 2 hours 30 minutes, 3 hours, 4 hours, 6 hours, 8 hours, 10 hours, 12 hours, and 16 hours after taking the test drug, and 24 hours after taking the drug on the 6th day). When participating in the cohort 5, pharmacokinetic blood collection was performed for 15 days (within 60 minutes before taking the test drug on the 3rd, 4th, and 5th days, within 60 minutes before taking the test drug on the 14th day, every 30 minutes, 1 hour, 1 hour 30 minutes, 2 hours, 2 hours 30 minutes, 3 hours, 4 hours, 6 hours, 8 hours, 10 hours, 12 hours, and 16 hours after taking the test drug, and 24 hours after taking the drug on the 15th day). When participating in the cohort 6, the pharmacokinetic blood collection was performed within 60 minutes before taking CT-G11 on the 3rd, 4th, and 5th days based on the administration at 8 am for 14 days, and the pharmacokinetic blood collection was performed within 60 minutes before taking CT-G11 on the 14th day and every 30 minutes, 1 hour, 1 hour 30 minutes, 2 hours, 2 hours 30 minutes, 3 hours, 4 hours, and 8 hours after the administration.

As the plasma concentration of the S(−)-cibenzoline succinate, a plasma concentration of the S(−)-cibenzoline succinate was measured from the pre-treated blood samples using LC-MS. As shown in Table 9, it was confirmed that three formulations were shown to exert the pharmacodynamically equivalent medicinal effect, and the minimum effective plasma concentration of about 100 to 150 ng/mL or more was maintained, the minimum effective plasma concentration being confirmed through the previously performed beagle dog non-clinical (in-vivo) experiment, and thus, the effect of the drug was maintained in the patients for 24 hours.

TABLE 9

| Pharmacodynamic analysis | Cohort 4 200 mg of S(−)-cibenzoline succinate once a day | Cohort 5 300 mg of S(−)-cibenzoline succinate once a day | Cohort 6 150 mg of racemic mixture cibenzoline succinate three times a day |
|---|---|---|---|
| Cmax (ng/mL) | 364.0 | 515.3 | 334.2 |
| AUC (h*ng/mL) | 3182.9 | 4299.3 | 4732.2 |
| Tmax (h) | 2.6 | 2.0 | 1.0 |
| Minimum effective plasma concentration (ng/mL) | 100 to 150 | 100 to 150 | 100 to 150 |

The invention claimed is:

1. A pharmaceutical formulation comprising from 150 mg to 450 mg of S(−)-cibenzoline or a pharmaceutically acceptable salt thereof;

wherein the pharmaceutical formulation includes an immediate release layer and an extended release layer;

wherein a weight ratio of the S(−)-cibenzoline or the pharmaceutically acceptable salt thereof contained in the immediate release layer relative to the S(−)-cibenzoline or the pharmaceutically acceptable salt thereof contained in the extended release layer is from 1:4 to 1:1; and wherein the pharmaceutical formulation satisfies following biphasic dissolution profile in a dissolution test:

1) 30 to 50% of the total weight of the S(−)-cibenzoline or the pharmaceutically acceptable salt thereof is released within 30 minutes, and 2) thereafter, 90% or more of the total weight of the S(−)-cibenzoline or the pharmaceutically acceptable salt thereof is released within 12 hours.

2. The pharmaceutical formulation of claim 1, wherein an extended release agent is contained in the pharmaceutical formulation in an amount of about 5 to about 30% with respect to the total weight of the extended release layer.

3. The pharmaceutical formulation of claim 2, wherein a viscosity of the extended release agent is about 1,500 to about 200,000 centipoise (cps).

4. The pharmaceutical formulation of claim 2, wherein the extended release agent is selected from hydroxyethyl cellulose, hydroxypropyl methylcellulose, and a salt or derivative thereof, polyethylene oxide and a salt or derivative thereof, sodium carboxymethyl cellulose, carbomer, polyvinyl acetate, and a mixture thereof.

5. The pharmaceutical formulation of claim 1, wherein a disintegrant is contained in the pharmaceutical formulation in an amount of about 1 to about 10% with respect to the total weight of the immediate release layer.

6. The pharmaceutical formulation of claim 5, wherein the disintegrant is selected from carboxymethylcellulose calcium, pregelatinized starch, sodium starch glycolate, crospovidone (polyplasdone), croscarmellose sodium, low-substituted hydroxypropylcellulose, alginic acid, powdered cellulose, starch, sodium alginate, and a mixture thereof.

7. The pharmaceutical formulation of claim 1, wherein the immediate release layer contains:

(a-1) S(−)-cibenzoline or a pharmaceutically acceptable salt thereof, and (a-2) a disintegrant in an amount of about 1 to about 10% with respect to the total weight of the immediate release layer, and the extended release layer contains:

(b-1) S(−)-cibenzoline or a pharmaceutically acceptable salt thereof, and (b-2) an extended release agent in an amount of about 5 to about 30% with respect to the total weight of the extended release layer.

8. The pharmaceutical formulation of claim 7, wherein the immediate release layer contains:

(a-1) S(−)-cibenzoline or a pharmaceutically acceptable salt thereof in an amount of about 25% to about 40% with respect to the total weight of the immediate release layer; and (a-2) a disintegrant selected from carboxymethylcellulose calcium, pregelatinized starch, sodium starch glycolate, crospovidone (polyplasdone), croscarmellose sodium, low-substituted hydroxypropylcellulose, alginic acid, powdered cellulose, starch, sodium alginate, and a mixture thereof in an amount of about 1 to about 10% with respect to the total weight of the immediate release layer, and the extended release layer contains:

(b-1) S(−)-cibenzoline or a pharmaceutically acceptable salt thereof in an amount of about 30% to about 40% with respect to the total weight of the extended release layer; and (b-2) an extended release agent selected from hydroxyethyl cellulose, hydroxypropyl methylcellulose, and a salt or derivative thereof, polyethylene oxide and a salt or derivative thereof, sodium carboxymethyl cellulose, carbomer, polyvinyl acetate, and a mixture thereof in an amount of about 5 to about 30% with respect to the total weight of the extended release layer.

9. The pharmaceutical formulation of claim 7, wherein the immediate release layer or the extended release layer contains an excipient selected from microcrystalline cellulose, lactose monohydrate, hydroxypropylcellulose, magnesium stearate, colloidal silicon dioxide, lactose, dextrin, mannitol, sorbitol, starch, microcrystalline cellulose, calcium hydrogen phosphate, anhydrous calcium hydrogen phosphate, calcium carbonate, saccharides, polyvinylpyrrolidone, copovidone, gelatin, sucrose, methyl cellulose, ethyl cellulose, light anhydrous silicic acid, talc, stearic acid, and a mixture thereof.

10. The pharmaceutical formulation of claim 1, wherein in the pharmaceutical formulation, a plasma concentration [C] of the S(−)-cibenzoline or the pharmaceutically acceptable salt thereof is about 150 ng/ml or more for about 6 hours to about 18 hours out of 24 hours.

11. A pharmaceutical formulation for treating hypertrophic cardiomyopathy comprising the pharmaceutical formulation of claim 1.

12. A kit comprising the pharmaceutical formulation of claim 1 and instructions that instruct a patient to administer the pharmaceutical formulation once a day.

* * * * *